US009227057B2

(12) United States Patent
McElveen, Jr.

(10) Patent No.: US 9,227,057 B2
(45) Date of Patent: Jan. 5, 2016

(54) METHOD OF REMOTE MONITORING AND MODULATION OF MEDICAL APPARATUS

(76) Inventor: John T. McElveen, Jr., Raleigh, NC (US)

( * ) Notice: Subject to any disclaimer, the term of this patent is extended or adjusted under 35 U.S.C. 154(b) by 538 days.

(21) Appl. No.: 13/527,324

(22) Filed: Jun. 19, 2012

(65) Prior Publication Data
US 2012/0259385 A1    Oct. 11, 2012

Related U.S. Application Data

(63) Continuation of application No. 12/900,449, filed on Oct. 7, 2010, now abandoned.

(60) Provisional application No. 61/249,546, filed on Oct. 7, 2009, provisional application No. 61/302,126, filed on Feb. 6, 2010.

(51) Int. Cl.
*A61N 1/36*    (2006.01)
*G06F 19/00*    (2011.01)
(Continued)

(52) U.S. Cl.
CPC .......... *A61N 1/36032* (2013.01); *A61B 5/0022* (2013.01); *A61B 5/0031* (2013.01);
(Continued)

(58) Field of Classification Search
CPC ........... A61N 1/36032; A61N 1/37258; A61N 1/37264; A61N 1/37282; G06F 19/3406; G06F 19/3418
USPC ................................. 607/57, 59, 60
See application file for complete search history.

(56) References Cited

U.S. PATENT DOCUMENTS 5,915,091 A    6/1999 Ludwig et al.
6,386,882 B1   5/2002 Linberg
(Continued)

FOREIGN PATENT DOCUMENTS

EP    0898424 A2    2/1999
JP    2002-140576 A    5/2002
(Continued)

OTHER PUBLICATIONS

Bartlett, J., "H.323 Videoconferencing Network Bandwidth Analysis", Aug. 25, 1997, pp. 1-7, Publisher: NSD Engineering, Picture Tel Corporation.
(Continued)

*Primary Examiner* — Allen Porter, Jr.
(74) *Attorney, Agent, or Firm* — Hultquist, PLLC; Steven J. Hultquist; Mary B. Grant

(57) ABSTRACT

A method of remotely programming a cochlear implant comprises, at a remote patient location attendable by a patient, operatively coupling the cochlear implant to a remote programming computer configured to generate a signal to program the cochlear implant. The patient is provided with a remote video conferencing system configured to receive video and audio of a local operator remotely programming the cochlear implant to enable the patient to both hear and see a face of the local operator during programming to enable the patient to read lips of the local operator to supplement hearing of the patient in communicating with the local operator. At a local programming location, the local operator accesses a local programming computer that is communicationally coupled to the remote programming computer by which the local operator at the local programming location can interactively control the remote programming computer to program the cochlear implant.

20 Claims, 3 Drawing Sheets

(51) Int. Cl.
*A61N 1/372* (2006.01)
*A61B 5/00* (2006.01)
*H04R 25/00* (2006.01)

(52) U.S. Cl.
CPC ........ *A61N1/37264* (2013.01); *A61N 1/37282* (2013.01); *H04R 25/70* (2013.01); *G06F 19/3418* (2013.01); *H04R 25/30* (2013.01); *H04R 2225/55* (2013.01)

(56) References Cited

U.S. PATENT DOCUMENTS

| | | |
|---|---|---|
| 6,662,051 B1 | 12/2003 | Eraker et al. |
| 6,669,631 B2 * | 12/2003 | Norris et al. ................ 600/300 |
| 7,383,088 B2 | 6/2008 | Spinelli et al. |
| 2002/0123673 A1 | 9/2002 | Webb et al. |
| 2003/0041866 A1 | 3/2003 | Linberg et al. |
| 2003/0088290 A1 | 5/2003 | Spinelli et al. |
| 2003/0117580 A1 | 6/2003 | Franz et al. |
| 2003/0120324 A1 | 6/2003 | Osborn et al. |
| 2004/0010297 A1 | 1/2004 | Ripart et al. |
| 2005/0081158 A1 | 4/2005 | Hwang |
| 2005/0159787 A1 | 7/2005 | Linberg et al. |
| 2005/0283198 A1 | 12/2005 | Haubrich et al. |
| 2006/0161214 A1 | 7/2006 | Patel |
| 2006/0247709 A1 | 11/2006 | Gottesman et al. |
| 2007/0130287 A1 * | 6/2007 | Kumar et al. ................ 709/217 |
| 2008/0140161 A1 | 6/2008 | Goetz et al. |
| 2008/0140162 A1 | 6/2008 | Goetz et al. |
| 2009/0292340 A1 * | 11/2009 | Mass et al. ................ 607/60 |
| 2010/0183163 A1 | 7/2010 | Matsui et al. |
| 2011/0082520 A1 | 4/2011 | McElveen, Jr. |

FOREIGN PATENT DOCUMENTS

| | | |
|---|---|---|
| JP | 2004-7482 A | 1/2004 |
| JP | 2005-518856 A | 6/2005 |
| JP | 2006-191498 A | 7/2006 |
| JP | 2008-22878 A | 2/2008 |
| JP | 2008-306535 A | 12/2008 |
| WO | 9842407 A1 | 10/1998 |
| WO | 2008069896 A2 | 6/2008 |

OTHER PUBLICATIONS

Bashshur, R., "Telemedicine and Health Care", "Telemedicine Journal and e-Health", Mar. 2002, pp. 5-13, vol. 8, No. 1.

Olifer, V., "Different Flavours of VPN: Technology and Applications", Mar. 2007, pp. 1-28, Publisher: The JNT Association.

Wilson, B., et al., "Cochlear implants: A remarkable past and a brilliant future", "Hearing Research", Jun. 22, 2008, pp. 3-21, vol. 242.

* cited by examiner

METHOD OF REMOTE MONITORING AND MODULATION OF MEDICAL APPARATUS

CROSS-REFERENCE TO RELATED APPLICATIONS

The benefit of priority of U.S. patent application Ser. No. 12/900,449 filed on Oct. 7, 2010 in the name of John T. McElveen, Jr. for "SYSTEM FOR REMOTE MONITORING AND MODULATION OF MEDICAL APPARATUS," is hereby claimed under the provisions of 35 U.S.C. §120, and the benefit of priority of U.S. Provisional Patent Application 61/249,546, filed Oct. 7, 2009 in the name of John T. McElveen, Jr. for "SYSTEM FOR REMOTE MONITORING AND MODULATION OF COCHLEAR IMPLANTS," and the benefit of priority of U.S. Provisional Patent Application 61/302,126, filed Feb. 6, 2010 in the name of John T. McElveen, Jr. for "SYSTEM FOR REMOTE MONITORING AND MODULATION OF COCHLEAR IMPLANTS," also are hereby claimed under the provisions of 35 U.S.C. §119(e). The disclosures of said U.S. patent application Ser. No. 12/900,449 and U.S. Provisional Patent Applications 61/249,546 and 61/302,126 are hereby incorporated herein by reference, in their respective entireties, for all purposes.

FIELD OF THE INVENTION

The present invention relates to a system and method for remotely monitoring and modulating programmable medical apparatus, e.g., programmable audiological medical devices such as cochlear implants and other programmable hearing devices, utilizing an interactive communications network such as the Internet.

BACKGROUND

Since its inception in the late 1960s and early 1970s, telemedicine has continued to evolve as an acceptable and effective modality for therapeutic intervention. The initial era of broadcasting or posting non-integrated audio and visual data has given way to digitization and simultaneous transmission of interleaved audio and video data streams delivered at higher speeds over private networks (Bashshur, R., Telemedicine and Health Care, Telemed J E Health 2002; 8: 5-12). This in turn has led to lower cost and even faster transmission implementations of telemedicine utilizing interactive global communication networks such as the Internet.

The present invention utilizes the potential of such high speed, high bandwidth interactive global communications networks for remotely monitoring and modulating programmable medical apparatus, including programmable audiological medical devices such as cochlear implants, in-ear hearing aids, bone conduction hearing aids, implantable hearing aids, auditory feedback speech therapy devices, voice-activated medical apparatus, and the like. In a wide variety of applications, the invention achieves a substantial advance in the art, by markedly enhancing the performance and patient experience of medical apparatus.

SUMMARY

The present disclosure relates to apparatus and method for remotely monitoring and modulating programmable medical apparatus.

In one aspect, the disclosure relates to a system for remotely programming a programmable medical apparatus, comprising a user location attendable by a user of the programmable medical apparatus, and a remote programming location that is communicationally coupled to the remote programming location by an interactive communication capability by which the remote programming location can communicatively program the programmable medical apparatus.

The disclosure in another aspect relates to a system for remotely programming a programmable medical apparatus, comprising a digital interactive communications network including an encrypted VPN tunnel interconnecting respective computers and video conferencing devices at a programming site and a remote programmed site, with VNC linkage of the interconnected computers, wherein said computers are arranged for programming the programmable apparatus from the programming site, with at least 1 megabit/second connection in both directions of interconnection, whereby audio and video signals are synchronized for the programming the programmable apparatus, e.g., cochlear implants, in-ear hearing aids, bone conduction hearing aids, implantable hearing aids, auditory feedback speech therapy devices, voice-activated medical apparatus, and the like.

A further aspect of the disclosure relates to a method for remotely programming a programmable medical apparatus, comprising use of the system as described above.

In another, specific aspect, the disclosure relates to a system for remotely programming a cochlear implant, comprising a digital interactive communications network including an encrypted VPN tunnel interconnecting respective computers and video conferencing devices at a programming audiologist site and a remote audiologist patient site, with VNC linkage of the interconnected computers, wherein said computers are arranged for programming the cochlear implant from the programming audiologist site, with at least 1 megabit/second connection in both directions of interconnection, whereby audio and video signals are synchronized for the programming the cochlear implant.

In another aspect, the disclosure relates to a method for remotely programming a cochlear implant, comprising use of the system as described above.

Other aspects, features and embodiments of the disclosure will be more fully apparent from the ensuing description and appended claims.

DETAILED DESCRIPTION

Figure 1:
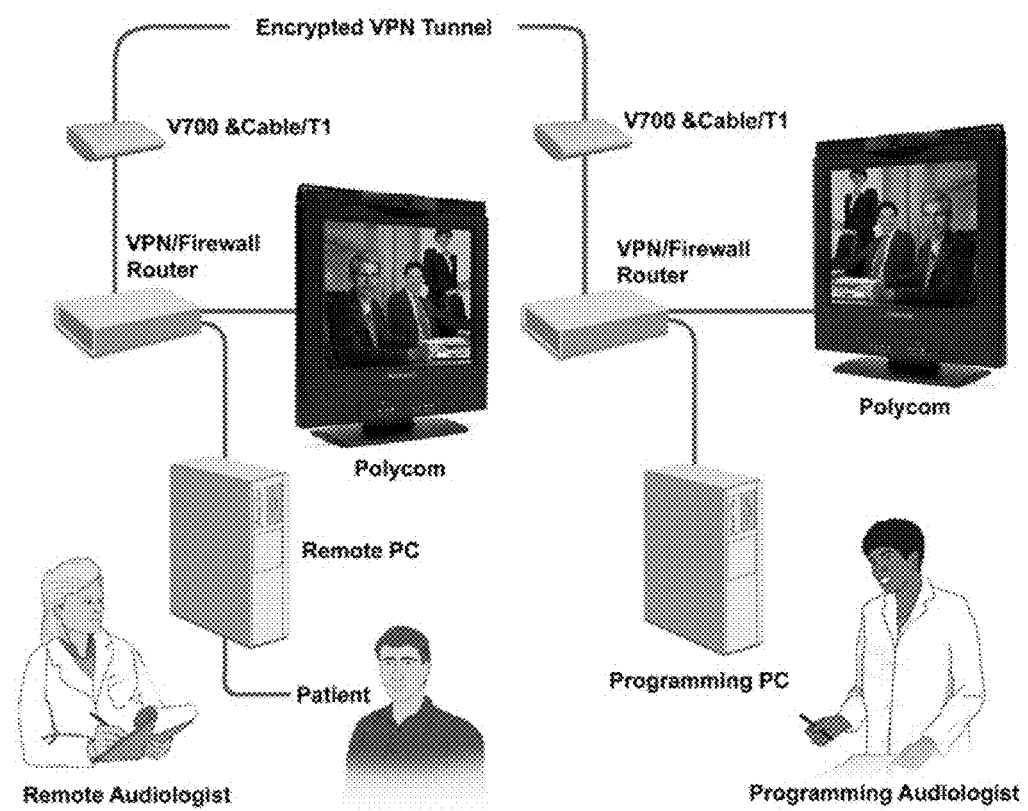
FIG. 1 is a schematic representation of a remote programming system for remote audiological monitoring and programmatic control of a cochlear implant in a human patient, according to one embodiment of the disclosure.

The present disclosure relates to a system and method for remote programming of medical apparatus.

While the disclosure is set out hereinafter primarily in application to cochlear implants in human patients, as illustrative of various medical apparatus with which the invention can be usefully implemented, it will be recognized that the utility of the invention extends to and encompasses a wide variety of apparatus whose monitoring, calibration and operation are amenable to remote intervention as herein generally described.

Such apparatus and devices include, without limitation, cochlear implants, in-ear hearing aids, bone conduction hearing aids, implantable hearing aids, auditory feedback speech therapy devices, such as the choral feedback systems of U.S. Pat. Nos. 5,961,443; 6,754,632; 7,031,922; and 7,591,779, voice-activated medical apparatus, and the like.

The disclosure will now be directed to an illustrative implementation to cochlear implants.

The invention in such illustrative cochlear implant implementation may be configured in a variety of arrangements, utilizing specifically programmed computers and specialized videoconferencing equipment installations at respective locations of a programming audiologist (programming location) and a remote patient (patient location). The invention thereby affords cochlear implant centers with a means to access patients who may otherwise be unable or unwilling to travel to the cochlear implant center for programming or mapping of their cochlear implant devices.

The system and method of the invention enable efficient programming of cochlear implants, in a safe and economic manner that ensures patient privacy and real-time access with minimal signal transmission and reception issues.

The invention in one implementation utilizes a remote programming arrangement in which the Internet or other interactive global communication network is employed to access a remote desktop computer for programming, and for sending and receiving synchronized, minimally delayed audio/visual signals. The system is programmatically arranged to insulate the cochlear implant patient from a corrupt signal or electrical surge during the cochlear implant mapping process. A desktop computer is provided, programmed with cochlear implant programming software, to generate a signal from the remote computer to the patient's cochlear implant.

In order to avoid signal issues due to electrical surges, all equipment utilized in programming cochlear implant patients in accordance with the invention, including routers and Internet switches, is desirably grounded, connected to surge protection equipment, and provided with battery backup.

For the purpose of ensuring patient confidentiality, and complying with the Health Insurance Portability and Accountability Act (HIPPA) of 1996 governing remote programming techniques that interface with the public Internet and involve electronic transmission of protected health information, all data transmitted in the operation of the system is encrypted and sent in a special format safeguarding information. The data may be secured by establishing a virtual private network (VPN) between the cochlear implant patient remote site and the cochlear implant center programming site. Such VPN creates an encrypted "tunnel" (transmission path) through which all data flowing between the remote patient site and local programming site are secure.

Although HIPPA-compliant encrypted communications are contemplated to comply with applicable regulatory requirements, it is recognized that non-encrypted communications may be employed in various implementations of the invention.

Once the VPN link between the two sites is established, the cochlear implant audiologist at the local programming site assumes control of the remote computer using a Virtual Network Computing (VNC) programming software package. VNC is a graphical desktop sharing application using RFB protocol for remote control of another computer, which transmits keyboard and mouse data from one computer to another, and receives graphical screen feedback from such other computer, over any suitable interactive communications that work, such as the Internet. Since VNC is platform-independent, the local programming site and remote patient site may utilize computers employing different operating systems.

Thus, establishment of the VPN link between the remote patient site and local programming site enables a cochlear implant audiologist at the local site to take control of the remote computer using the VNC application, while letting both sites simultaneously view the computer screen and video link. The remote site may include presence of a non-implant audiologist to effectuate the programming of the cochlear implant device in the patient.

Simultaneous viewing of the computer screen via the cochlear implant audiologist and the non-implant audiologist is thereby accommodated. This has two benefits. If there are any communication errors or problems with the remote programming procedure, the remote non-implant audiologist attending the patient can immediately take control of the programming computer. In addition, the simultaneous viewing enables training of the non-implant audiologist to be carried out, since the audiologist at the remote patient site is able to view the programming technique utilized by the cochlear implant audiologist at the local programming site.

The system is arranged so that the audio and visual signals between the respective sites are synchronized and minimally delayed. It is generally undesirable to operate the audio, video and computer programming software simultaneously via the computer, since delays in signal transition may become unacceptable. Hearing impaired patients rely, in part, on lip reading, and synchronization of the audio and video signal is therefore particularly important.

Consequently, the system preferably uses a videophone system that bundles both audio and video signals so that both signals are synchronized with one another. Because the videophones transmit information via the Internet, the VPN used to transmit this data provides a secure arrangement protecting the data and privacy of the patient. Any suitable videophone system can be employed. Commercially available videophone systems that may be satisfactorily utilized in the practice of the present invention include the D-Link i2eye Broadband Desktop Videophone (DVC 2000), and the Polycom® V700™ video conferencing system.

The human eye perceives real-time, smooth motion as 30 frames per second (fps). Transmission at this speed requires a large bandwidth, which is not cost effective. To compensate, computers compress the signal at the origin and decompress it at the receiving site. If the video and audio compression is being performed on the same computer, it competes with the computer's other applications, and thus videophones are preferred in the practice of the present invention. The audio and video information on the videophone runs independently and does not compete with the applications running on the cochlear implant computer.

It is desired that the image resolution on the videophone provide smooth motion visualization, with good field of view characteristics.

The aforementioned Polycom® V700™ video conferencing system uses a bandwidth of 768 kilobits/sec (kbps) and interleaves video and audio streams, providing synchronized delivery. Such bandwidth (768 kbps) is consistent with most small business Internet connection speeds. The Polycom® V700™ device also has its own IP address, which allows routers/switches to prioritize such device over other network devices. The Polycom® V700™ video conferencing device requires 768 kbps in both directions for optimal performance, and can use a T1 line or other suitable connection.

In utilizing the interconnected computers and video conferencing equipment, good "site to site" connection is desirable to minimize signal delay and enhance audio/visual quality. Internet connections are adequate to satisfy such operational parameters. A commercial grade Internet connection should be used by both remote and local sites when performing remote programming, such as the T1 line above mentioned. A consistent 1 megabit/sec connection in both directions is the minimum required for high performance.

In order to check for lost packets or long network delays that would otherwise adversely affect the audio/video signal between the remote and local sites, suitable software, e.g., PingPlotter (Messoft, LLC) may be employed. PingPlotter is a network troubleshooting tool for Windows® that uses a combination of "tracerrout", "ping", and "whois" to demonstrate the "hops" on the Internet the signal packets are taking, and the length of time required. It may be preferred to utilize the same Internet service provider (ISP) for the local and remote sites, in order to better ensure that transmitted data packets stay on the ISP's "back-bone". This minimizes the number of "hops" and provides better and more consistent transmission times.

In tests of the inventive remote programming system, patients appeared to genuinely appreciate the convenience of having their cochlear implant placed and programmed locally (at the patient site remote from the cochlear implant audiologist site). In a specific test, involving patients whose devices were remotely programmed in Greenville, S.C. and locally in Raleigh, N.C., no significant differences were found between the respective location cohorts in the scores for the HINT sentence test or the CNC word test. These results show the equivalence of fitting cochlear implants locally or remotely, with proper equipment, communication links, and safeguards.

Thus, the present invention enables remote programming of cochlear implant patients using the Internet or other interactive data communications networks. The empirical tests of the invention demonstrate that patients programmed remotely have done as well as locally programmed patients. It therefore is possible to conduct surgical procedures and cochlear implant mapping in remote locations, and to subsequently program implants remotely via Internet data, voice and video transmission, with or without the assistance of an audiologist or other caregiver at the patient site. The invention enables effective and high quality cochlear implant mapping and programming to be performed remotely at satellite clinics via an Internet or other digital interactive data/voice/video communication networks. The invention also contemplates the establishment of remote sites that are arranged for self-testing with little or no technical medical assistance being required, such as sites at which an audiologist and/or other medical personnel are replaced with automated systems that are interactive with the patient and the remote monitoring and control site. In still other embodiments, the monitoring and calibration operations may be effected by a mobile monitoring and calibration assembly, which may be fixed or motive in character, such as a vehicular platform that is driven or trailered to a specific location, e.g., an urban area, a remote area, or a location having a suitable communications node, and operated using interactive networks, wireless communications such as a wireless telephony network for smart phone usage, satellite communications, or other communication modalities.

It will also be appreciated that the invention is susceptible of implementation. In embodiments in which synchronized audio and video signals are non-essential to the programming of the programmable medical apparatus, and in which non-synchronized audio signals can be used, or in which optoelectronic signal transmission can be utilized for the remote programming, or in which other signal transmission modalities may be employed to effect the programming operation.

Thus, the invention may be practiced to carry out remote programming with or without a VPN, and with or without audio and visual signal synchronization, such as by use of interconnected computers at the respective patient and monitoring sites.

The invention contemplates application using in vivo monitoring or ex vivo monitoring programmable devices that are susceptible to remote or otherwise automated programming, including calibration and adjustment, such as by running selected or automated testing routines providing input to a monitoring module that responsively reprograms the device, to ensure enhanced operational capability of such device. The testing routines may be of a routine maintenance character, or may be selected by the patient, central processor, or medical personnel to determine whether operation of the programmable devices within allowable tolerances, or alternatively, such device requires adjustment, recalibration or the like.

Programmable devices to which the system and method of the present invention can be applied include, without limitation, audiological equipment, pacemakers, intelligent prosthetics, neural prostheses of a programmable character, hearing aids, implantable pumps, e.g., for insulin administration, deep brain stimulation apparatus, swallowable monitoring and diagnostic capsules containing programmable devices, other programmable interfaces utilized in therapeutic intervention for treatment of human or veterinary subjects, health status monitors, e.g., devices transmitting telemetry data out of a human or animal body, and any other programmable medical, therapeutic, or diagnostic device.

The invention may be practiced with any appropriate modes of communication between the remote monitoring site and the patient site, and as mentioned, devices can be remotely programmed over the Internet, or via other interactive communications networks, with or without virtual private network (VPN) and/or encryption of communications.

The features and advantages of the invention are more fully shown by the following non-limiting example.

EXAMPLE

An experimental satellite cochlear implant program was established in Greenville, S.C., over 250 miles from a tertiary cochlear implant center in Raleigh, N.C. Medical and audiology licenses to practice in South Carolina were obtained by the implant surgeon and the cochlear implant audiologist.

Both sites were equipped with a desktop computer and commercially approved cochlear implant programming hardware and software. The following additional layer of hardware and software technology was also installed to enable the remote programming capability: (a) a commercial grade Internet connection was installed in both locations; (b) for security concerns, routers with Virtual Private Network (VPN) capabilities (Netgear® ProSafe VPN Firewall Model FVS 318, San Jose, Calif.) were installed to provide secure communication between sites; (c) Virtual Network Computing (VNC) remote desktop software was installed and configured at both sites, allowing the computer in Raleigh to control the desktop in Greenville, S.C.; and (d) a commercial video conferencing system, the Polycom® V700™ (Polycom® Inc., Andover, Mass.) was installed in the Raleigh and Greenville offices, in an arrangement as schematically represented in FIG. 1.

In order to minimize inconvenience and cost for the cochlear implant patients, the cochlear implant evaluation, cochlear implant surgery, and cochlear implant mapping were all performed in Greenville, S.C.

An experienced cochlear implant audiologist from the tertiary cochlear implant center in Raleigh trained a "non-cochlear implant" audiologist in Greenville to perform the initial evaluation. In addition to standard diagnostic audiological testing, the initial evaluation included Hearing in Noise Test (HINT) sentences and Consonant/Nucleus/Consonant (CNC) word lists. It is noted that other speech reception measures such as Freiburg could alternatively, or additionally, be utilized. The cochlear implant audiologist directly screened the patients for cochlear implant candidacy in Greenville on a quarterly basis, and the patients were then evaluated by the otologist for possible cochlear implantation. Informed consents were obtained, and those candidates who were surgical candidates underwent cochlear implantation at Greenville Memorial Hospital, in Greenville, S.C.

The patients were scheduled for programming of their implant at one month, three months, six months, and twelve months, postoperatively. HINT and CNC scores were obtained at that time. The cochlear implant was programmed using the following protocol:

(i) The audiologist in Greenville brought the cochlear implant programming system online and readied it prior to the patient arriving, confirming the audio and video connection with the Raleigh office.

(ii) The Raleigh audiologist who performed the implant programming opened the VNC remote desktop connection in order to take over the Cochlear implant programming computer in Greenville.

(iii) The patient was then brought into the Greenville cochlear implant programming room, and was accompanied by the Greenville audiologist at all times during the programming procedure. The audiologist with the patient observed the entire procedure, and was available to take control of the programming computer in Greenville if necessary.

(iv) The VNC remote desktop software transmitted keystrokes and mouse movements from the Raleigh computer to the Greenville computer, and the Greenville computer returned screen updates to the computer in Raleigh. Although the cochlear implant audiologist inputted the commands for programming in Raleigh, the application on the computer in Greenville actually programmed the implant.

Using the above protocol, patients had a standard post cochlear implant test battery performed at one, three, six and twelve months after implantation. Postoperative HINT and CNC word scores for the seven post-lingually deafened patients who had undergone remote mapping and programming of their Nucleus Freedom cochlear implant were compared with the scores of seven post-lingually deafened patients who had similar durations of deafness, and who had been programmed in Raleigh by the same audiologist over a six to twelve month period. This group also had the Nucleus Freedom cochlear implant.

In the Greenville group, there were four males and three females ranging in age from 15 years to 87 years. Excluding the 15 year old patient, the mean age of the Greenville group was 67 years, with only one year difference from the seven Raleigh patients ranging in age from 54 to 79 years, with a mean age of 68 years. The Raleigh group consisted of one male and six females. Each of the subjects was implanted with the Freedom™ cochlear implant (Cochlear Corporation; Englewood, Colo.). The cochlear implant audiologist assessed the times required for both remote and on-site programming/mapping.

Results

All surgeries were performed without complications. Each of the patients' implants was successfully programmed at the Greenville site by the cochlear implant audiologist over 250 miles away.

None of the patients experienced apparent signal corruption or any AC electrical surge during programming. Upgrading from the D-Link i2eye Broadband Desktop Videophone (D-Link: DVC 2000; Taiwan) to the Polycom® V700™ video conferencing system resulted in some experience of signal interruption. Using PingPlotter, a network troubleshooting and diagnostic tool for Windows, the problem was traced to the router in Greenville. This was rectified by installing a T1 line, prioritizing the video signal, and removing the D-Link settings associated with the router. The "round trip" signal time between Raleigh and Greenville was approximately 58 msec.

The commercial grade Internet connection, and the hardware and software used for remote programming, proved reliable. The network latency issues related to remote programming did not interfere with the mapping, and the audiologist performing the programming could accurately observe patient responses. The patient and non-implant audiologist were also able to observe the implant audiologist during the implant programming procedure.

Figure 2A:
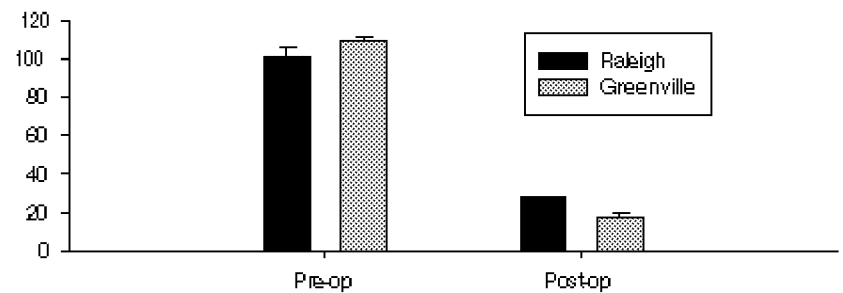
FIGS. 2A, 2B and 2C are graphs showing preoperative and postoperative audiological results, comparing remotely programmed cochlear implant patients in Greenville, S.C., USA with a similar group of locally programmed cochlear implant patients in Raleigh, N.C., USA.
Figure 2B:
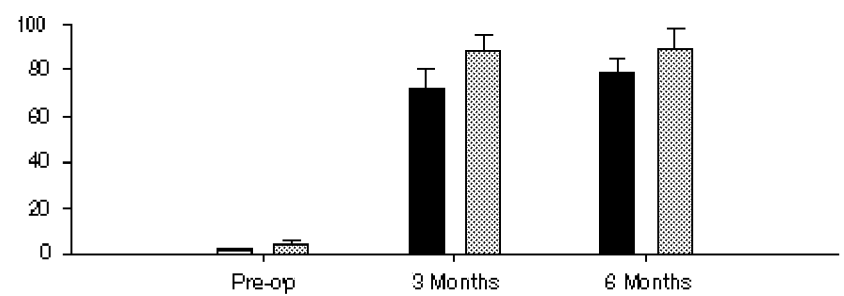
Figure 2C:
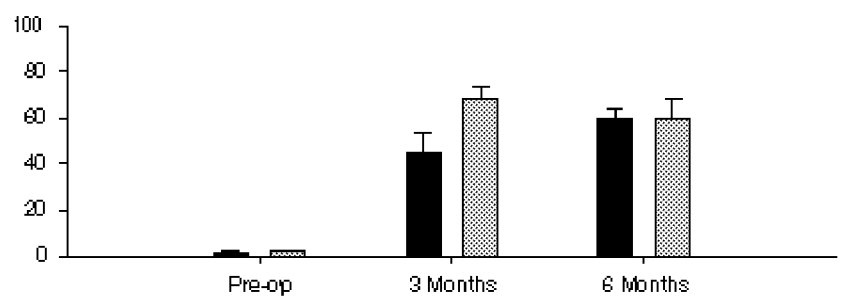

The preoperative and postoperative audiological test results for the Greenville patients are presented in Table 1, and the results from the Raleigh patients are presented in Table 2. FIG. 2 shows comparisons between the Raleigh and Greenville cohorts for pure tone averages (PTAs) for the pre- and post-operative intervals (FIG. 2A); recognition of the HINT sentences for the pre-operative, 3 month, and 6 month intervals (FIG. 2B); and recognition of the CNC words for those same intervals (FIG. 2C). Selection of the pre-operative, 3 month, and 6 month intervals allowed inclusion of the maximum number of tested subjects for the two measures of speech reception. All seven of the Raleigh subjects are included in panels (B) and (C), and the same five Greenville subjects (subjects G3 through G7) are included in each of those panels. All seven subjects from each of the cohorts are included in panel (A).

TABLE 1

OUTCOME MEASURES FOR GREENVILLE COCHLEAR IMPLANT RECEIPENTS

|  | G1 | G2 | G3 | G4 | G5 | G6 | G7 | Mean |
|---|---|---|---|---|---|---|---|---|
| Pre-Op PTA | 109 | 101 | 101 | 105 | 106 | 120 | 120 | 108.8571 |
| Aided Post-Op PTA | 18 | 16 | 29 | 13 | 10 | 18 | 15 | 17 |
| Ear Implanted | R | R | L | R | R | L | R |  |
| Pre-Op HINT score | 1 | 6 | 1 | 1 | 11 | 5 | 1 | 3.714286 |

TABLE 1-continued

OUTCOME MEASURES FOR GREENVILLE COCHLEAR IMPLANT RECEIPENTS

|  | G1 | G2 | G3 | G4 | G5 | G6 | G7 | Mean |
|---|---|---|---|---|---|---|---|---|
| Pre-Op CNC score | 1 | 1 | 0 | 1 | 2 | 4 | 1 | 1.428571 |
| 1 month HINT score | 55 | 32 | 88 | 57 | 84 | no show | no show | 63.2 |
| 3 month HINT score | no show | 88 | 96 | 62 | 99 | 96 | 89 | 88.33333 |
| 6 month HINT score | 54 | NS | 99 | 54 | 100 | 99 | 96 | 83.66667 |
| 12 month HINT score | 82 | 87 | 100 | NA | 99 | NA | 94 | 92.4 |
| 1 month CNC score | 12 | 0 | 64 | 34 | 38 | no show | no show | 29.6 |
| 3 month CNC score | no show | 70 | 72 | 62 | 82 | 74 | 49 | 68.16667 |
| 6 month CNC score | 22 | NS | 74 | 36 | 76 | 72 | 40 | 53.33333 |
| 12 month CNC score | 18 | 60 | 84 | NA | 82 | NA | 66 | 62 |

TABLE 2

OUTCOME MEASURES FOR Raleigh COCHLEAR IMPLANT RECEIPENTS

|  | R1 | R2 | R3 | R4 | R5 | R6 | R7 | Mean |
|---|---|---|---|---|---|---|---|---|
| Pre-Op PTA | 108 | 113 | 80 | 80 | 106 | 110 | 109 | 100.8571 |
| Aided Post-Op PTA | 26 | 25 | 28 | 31 | 28 | 30 | 26 | 27.71429 |
| Ear Implanted | L | R | R | L | R | L | R |  |
| Pre-Op HINT score | 2 | 4 | 0 | 0 | 0 | 0 | 0 | 0.857143 |
| Pre-Op CNC score | 0 | 4 | 0 | 0 | 0 | 0 | 0 | 0.571429 |
| 1 month HINT score | 75 | 73 | 49 | 65 | 95 | 30 | 2 | 55.57143 |
| 3 month HINT score | 75 | 84 | 83 | 61 | 100 | 74 | 24 | 71.57143 |
| 6 month HINT score | 88 | 80 | 84 | 78 | 100 | 78 | 47 | 79.28571 |
| 12 month HINT score | 88 | 97 | 73 | 73 | 99 | NA | 62 | 82 |
| 1 month CNC score | 50 | 38 | 20 | 38 | 64 | 16 | 0 | 32.28571 |
| 3 month CNC score | 62 | 46 | 26 | 44 | 84 | 42 | 6 | 44.28571 |
| 6 month CNC score | 70 | 72 | 40 | 50 | 74 | 60 | 48 | 59.14286 |
| 12 month CNC score | 70 | 66 | 50 | 28 | 90 | NA | 58 | 60.33333 |

Selection of the 3 and 6 month intervals also was guided by the observation that speech test scores for adult cochlear implant patients are generally asymptotic at 3-6 months of experience with the devices (Wilson B S, Dorman M F, Cochlear implants; a remarkable past and a brilliant future, Hearing Research 242:3-21, 2008). Thus, these intervals are especially useful "end points" for assessing possible differences between cohorts or device variables.

Each set of bars in FIG. 2 was compared with at test to evaluate the significance of possible differences. A p value of 0.05 or lower was regarded as indicating a significant difference.

None of the comparisons was significant except the difference between cohorts for the post-operative measures of PTAs ($p<0.001$). The difference in the means for the CNC word test at the 3 month interval was not statistically significant ($p=0.083$).

With the one exception, the results between the Greenville and Raleigh cohorts were statistically indistinguishable. That one exception is not an important difference, as the value for the post-operative PTA is arbitrary in the sense that a wide range of PTAs can be specified by the fitting audiologist through choices of settings for thresholds and most comfortable loudness levels for each of the electrodes in the implant and for the overall gain or sensitivity of the speech processor. Small changes in these settings sometimes can produce relatively large changes in the PTAs. The effect of the settings produced a slightly lower mean PTA for the Greenville cohort compared with the Raleigh cohort.

In addition, there was no substantial difference in time commitment with programming the patients in Greenville, as compared to the patients in Raleigh. Indeed, the cochlear implant audiologist's time spent with the patient in Greenville was more focused, with less tangential discussion.

Thus, the postoperative HINT and CNC word scores for the seven patients who had undergone remote mapping and programming of their cochlear implant were compared with the mean scores of seven patients who had been programmed by the same audiologist over a twelve month period, with the times required for remote and direct programming being compared, and the quality of the Internet connection assessed using standardized measures for remote programming performed via VPN with separate software programs used for video and audio linkage.

The results show that all seven patients were programmed successfully via remote connectivity. No untoward patient experiences were encountered. No statistically significant differences could be found in comparing postoperative HINT and CNC word scores for patients who had undergone remote programming versus a similar group of patients who had their cochlear implant programmed directly. Remote programming did not require a significantly longer programming time for the audiologist with these seven patients.

It is therefore concluded that remote programming of a cochlear implant can be performed safely with the system and method of the present invention, without any deterioration in the quality of the programming. This ability to remotely program cochlear implant patients provides the potential to extend cochlear implantation to underserved areas in the U.S. and elsewhere.

Figure 3:
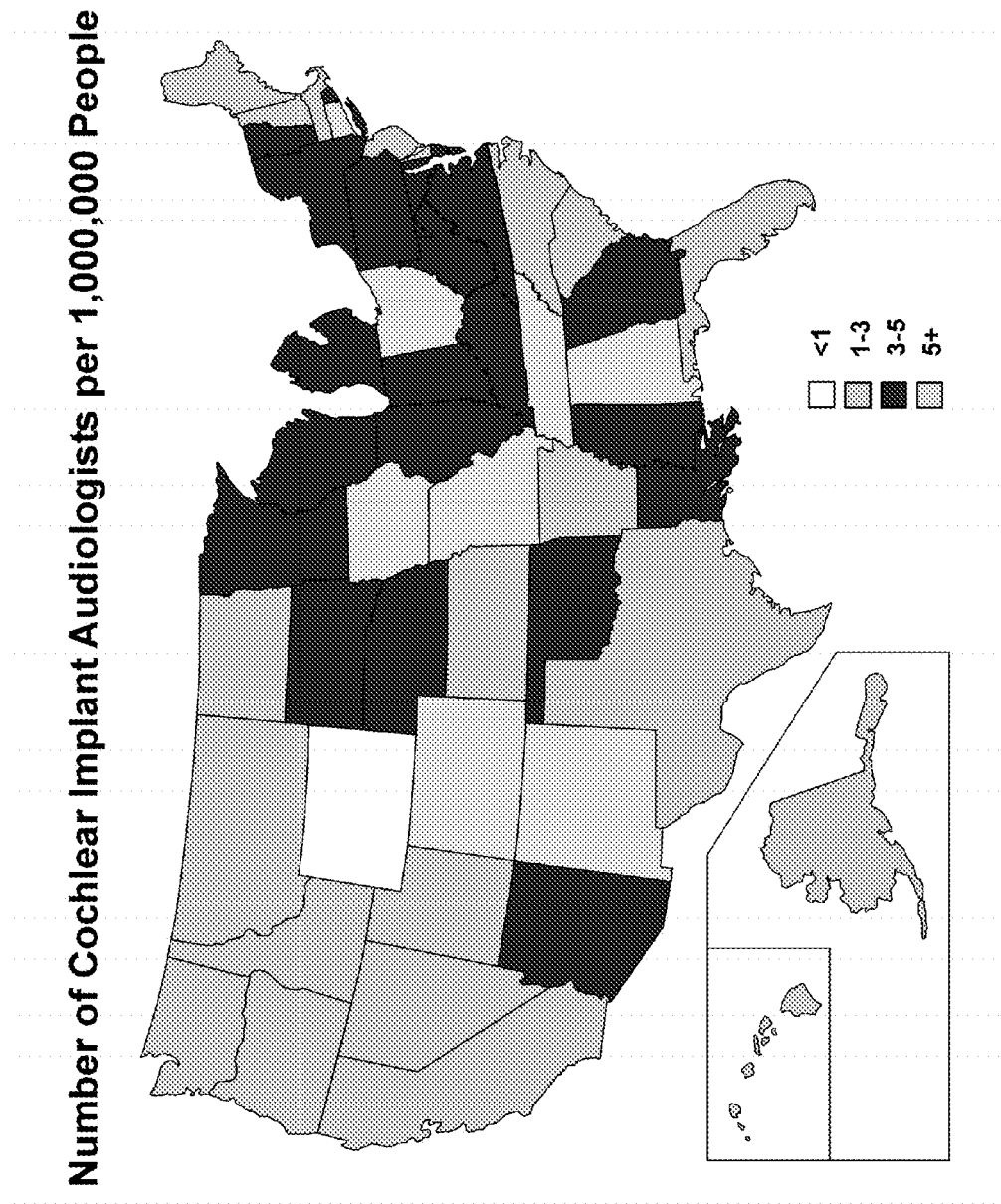
FIG. 3 is a graphical depiction of a map of the United States, showing a current distribution of cochlear implant audiologists in the United States.

The invention extends the reach of a cochlear implant audiologist to patients who may not be able or willing to travel to a tertiary cochlear implant center. As shown in the map depicted in FIG. 3, there is substantial disparity in the number of cochlear implant audiologists in a given region. Globally, a similar or even greater disparity exists, particularly in underdeveloped countries. In an empirical study to demonstrate the efficacy of the system and method of the present invention, patients were programmed over 250 miles away from a tertiary cochlear implant center. As Internet usage continues to expand, the apparatus and method of the invention may have potential for use in more remote areas. In another empirical test of the apparatus and method of the present invention, an Internet connection was utilized to program a cochlear implant patient remotely in Nigeria.

The invention thus is useful for remote programming of medical apparatus where the programming and the programmed locations are separated by distances measured in miles, e.g., at least 1, 5, 10, 20, 50, 100, 250, or 500 or more miles, in various embodiments of the invention.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of remotely programming a cochlear implant, comprising:
   at a remote patient location attendable by a patient using a cochlear implant:
   operatively coupling the cochlear implant to a remote programming computer configured to generate a signal to program the cochlear implant; and
   receiving, with a remote video conferencing system independent of the remote programming computer, video and audio of a local operator remotely programming the cochlear implant from a local programming location removed from the remote patient location to enable the patient to both hear and see a face of the local operator during programming of the cochlear implant by the local operator to enable the patient to read lips of the local operator to supplement hearing of the patient in communicating with the local operator during the programming;
   at the local programming location:
   providing the local operator with access to a local programming computer that is communicationally coupled to the remote programming computer at the remote patient location by an interactive communication capability having at least a 1 Mb/second communication rate in both directions by which the local operator at the local programming location can interactively control the remote programming computer to program the cochlear implant from the local programming location;
   transmitting, with a local video conferencing system independent of the local programming computer, the video and the audio of the local operator that is remotely programming the cochlear implant to the remote video conferencing system during the programming;
   wherein the video and the audio of the local operator are synchronized and the patient both is able to see and hear the local operator that is remotely programming the cochlear implant during the programming; and
   programming the cochlear implant while the video and audio of the local operator are synchronized,
   wherein the local programming computer and local video conferencing system of the local programming location are interconnected with the remote programming computer and remote video conferencing system of the remote patient location by an encrypted virtual private network (VPN),
   wherein the local programming computer and the remote programming computer are linked by a virtual network computing (VNC) link enabling simultaneous view of a graphical desktop output at the local programming computer and at the remote programming computer when the local operator interactively controls the remote programming computer, and
   wherein the local programming computer and local video-conferencing system and the remote programming computer and remote videoconferencing system are configured for remote mapping of the cochlear implant by the local operator comprising selection by the local operator, based on patient response, of settings for thresholds and most comfortable loudness levels for electrodes of the cochlear implant and for overall gain or sensitivity of a speech processor of the cochlear implant.

2. The method of claim 1, further comprising transmitting video and audio of the patient to the local operator to enable the local operator to observe responses of the patient during the programming.

3. The method of claim 1, wherein the interactive communication capability by which the local programming computer is communicationally coupled to the remote programming computer includes an interactive communications network that includes
   an Internet.

4. The method of claim 1, wherein the interactive communication capability includes a T1 line between the remote patient location and the local programming location.

5. The method of claim 1, wherein the remote video conferencing system and the local video conferencing system comprise devices that are physically separate from the remote programming computer and the local programming computer, wherein processing data used by the remote video conferencing system and the local video conferencing system does not impact processing performed by the remote programming computer and the local programming computer.

6. The method of claim 1, wherein the remote video conferencing system comprises a videophone device capable of synchronizing audio and video signals with one another.

7. The method of claim 6, wherein the local video conferencing system comprises a videophone device capable of synchronizing audio and video signals with one another.

8. A method of remotely programming a programmable audiological medical apparatus, comprising:
   at a remote patient location attendable by a patient using a programmable audiological medical apparatus:
   operatively coupling the programmable audiological medical apparatus to a remote programming computer configured to generate a signal to program the programmable audiological medical apparatus; and
   receiving, with a remote video conferencing system independent of the remote programming computer, video and audio of a local operator remotely programming the programmable audiological medical apparatus from a local programming location removed from the remote patient location to enable the patient to both hear and see the local operator during programming of the programmable audiological medical apparatus by the local operator and transmitting video and audio of the patient during the programming;
   at the local programming location:
   providing the local operator with access to a local programming computer that is communicationally coupled to the remote programming computer at the remote patient location by an interactive communication capability having at least a 1 Mb/second communication rate in both directions by which the local operator at the local programming location can interactively control the remote programming computer to program the programmable audiological medical apparatus from the local programming location;
   transmitting, with a local video conferencing system independent of the local programming computer, the video and the audio of the local operator that is remotely programming the programmable audiological medical apparatus to the remote video conferencing device during the programming and receiving the video and audio of the patient during the programming;
   wherein the video and the audio of the local operator are synchronized and the patient is able to see and hear the local operator and the local operator is able to see and hear the patient; and
   programming the programmable audiological medical apparatus while the video and audio of the local operator are synchronized, wherein the local programming computer and local video conferencing system of the local programming location are interconnected with the remote programming computer and remote video conferencing system of the remote patient location by an encrypted virtual private network (VPN), wherein the local programming computer and the remote programming computer are linked by a virtual network computing (VNC) link enabling simultaneous view of a graphical desktop output at the local programming computer and at the remote programming computer when the local operator interactively controls the remote programming computer, and wherein the local programming computer and local videoconferencing system and the remote programming computer and remote videoconferencing system are configured for remote mapping of the programmable audiological medical apparatus by the local operator comprising selection by the local operator, based on patient response, of settings for thresholds and most comfortable loudness levels for electrodes of the programmable audiological medical apparatus and for overall gain or sensitivity of a speech processor of the programmable audiological medical apparatus.

9. The method of claim 8, wherein the programmable audiological medical apparatus comprises an apparatus selected from the group consisting of in-ear hearing aids, bone conduction hearing aids, implantable hearing aids, auditory feedback speech therapy devices, and voice-activated medical apparatuses.

10. The method of claim 9, wherein the programmable audiological medical apparatus includes a cochlear implant.

11. The method of claim 8, wherein the interactive communication capability by which the local programming computer is communicationally coupled to the remote programming computer includes an interactive communications network that includes
an Internet.

12. The method of claim 8, wherein the interactive communication capability includes a T1 line between the remote patient location and the local programming location.

13. The method of claim 8, wherein the remote video conferencing system and the local video conferencing system comprise devices that are physically separate from the remote programming computer and the local programming computer, wherein processing data used by the remote video conferencing system and the local video conferencing system does not impact processing performed by the remote programming computer and the local programming computer.

14. The method of claim 8, wherein the remote video conferencing system comprises a videophone device capable of synchronizing audio and video signals with one another.

15. The method of claim 14, wherein the local video conferencing system comprises a videophone device capable of synchronizing audio and video signals with one another.

16. A method of remotely programming a cochlear implant, comprising:
providing a local operator at a local programming location with access to a local programming computer that is communicationally coupled to a remote programming computer at a remote patient location by an interactive communication capability by which the local operator at the local programming location can interactively control a remote programming computer operationally coupled to a cochlear implant to program the cochlear implant from the local programming location; and providing the local operator with a local video conferencing system comprising a first videophone device configured to transmit synchronized video and audio of the local operator that is remotely programming the cochlear implant to a remote video conferencing system comprising a second videophone device at the remote patient location during the programming; and the local operator programming the programmable apparatus from the local programming location while a patient using the cochlear implant is both able to see the face of and hear the local operator that is remotely programming the cochlear implant during the programming, wherein the local programming computer and local video conferencing system of the local programming location are interconnected with the remote programming computer and remote video conferencing system of the remote patient location by an encrypted virtual private network (VPN), wherein the local programming computer and the remote programming computer are linked by a virtual network computing (VNC) link enabling simultaneous view of a graphical desktop output at the local programming computer and at the remote programming computer when the local operator interactively controls the remote programming computer, and wherein the local programming computer and local videoconferencing system and the remote programming computer and remote videoconferencing system are configured for remote mapping of the cochlear implant by the local operator comprising selection by the local operator, based on patient response, of settings for thresholds and most comfortable loudness levels for electrodes of the cochlear implant and for overall gain or sensitivity of a speech processor of the cochlear implant.

17. The method of claim 16, further comprising:
operatively coupling the cochlear implant to a remote programming computer configured to generate a signal to program the cochlear implant; and
providing the patient with the second videophone configured to receive the video and audio of the local operator remotely programming the cochlear implant from the local programming location to enable the patient to both hear and see the face of the local operator during programming of the cochlear implant by the local operator to enable the patient to read lips of the local operator to supplement hearing of the patient in communicating with the local operator during the programming.

18. The method of claim 17, wherein the remote video conferencing system and the local video conferencing system are further configured to transmit video and audio of the patient to the local operator to enable the local operator to observe responses of the patient during the programming.

19. The method of claim 16, wherein the interactive communication capability by which the local programming computer is communicationally coupled to the remote programming computer is such that communications between the local operator and the patient comply with the Health Insurance Portability and Accountability Act (HIPPA) of 1996.

20. The method of claim 16, wherein the interactive communication capability has at least a 1 Mb/second communication rate in both directions.

* * * * *